United States Patent
Perraut et al.

(10) Patent No.: US 10,255,688 B2
(45) Date of Patent: Apr. 9, 2019

(54) ANALYSIS METHOD INCLUDING THE DETERMINATION OF A POSITION OF A BIOLOGICAL PARTICLE

(71) Applicants: COMMISSARIAT A L'ENERGIE ATOMIQUE ET AUX ENERGIES ALTERNATIVES, Paris (FR); BIOMERIEUX, Marcy-l'etoile (FR)

(72) Inventors: Francois Perraut, Saint Joseph de Riviere (FR); Pierre Joly, Grenoble (FR); Quentin Josso, Lyons (FR); Meike Kloster-Landsberg, Grafelfing (DE)

(73) Assignees: COMMISSARIAT A L'ENERGIE ATOMIQUE ET AUX ENERGIES ALTERNATIVES, Paris (FR); BIOMERIEUX, Marcy-l'etoile (FR)

( * ) Notice: Subject to any disclaimer, the term of this patent is extended or adjusted under 35 U.S.C. 154(b) by 0 days.

(21) Appl. No.: 15/526,092

(22) PCT Filed: Nov. 13, 2015

(86) PCT No.: PCT/EP2015/076530
§ 371 (c)(1),
(2) Date: May 11, 2017

(87) PCT Pub. No.: WO2016/075279
PCT Pub. Date: May 19, 2016

(65) Prior Publication Data
US 2017/0309036 A1    Oct. 26, 2017

(30) Foreign Application Priority Data
Nov. 13, 2014 (FR) ..................... 14 60947

(51) Int. Cl.
*G06T 7/55* (2017.01)
*G06T 15/10* (2011.01)
(Continued)

(52) U.S. Cl.
CPC ........... *G06T 7/55* (2017.01); *G01N 15/1434* (2013.01); *G01N 21/453* (2013.01);
(Continued)

(58) Field of Classification Search
CPC .............. G06T 7/55; G06T 7/97; G06T 15/10
See application file for complete search history.

(56) References Cited

U.S. PATENT DOCUMENTS

2010/0253762 A1* 10/2010 Cheong .................. G01B 9/021
348/31
2011/0141273 A1*  6/2011 Dubois ................. G02B 21/10
348/135
(Continued)

OTHER PUBLICATIONS

Zhang, Tong, and Ichirou Yamaguchi. "Three-dimensional microscopy with phase-shifting digital holography." Optics letters 23.15 (1998): 1221-1223. (Year: 1998).*
(Continued)

*Primary Examiner* — Bobbak Safaipour
(74) *Attorney, Agent, or Firm* — Oblon, McClelland, Maier & Neustadt, L.L.P.

(57) ABSTRACT

A method of analyzing a sample receiving a particle of interest, including: defining a reference point located on a first interface of the sample, or at a known distance from the sample, along the optical axis of the optical system; acquiring a reference image transmission of the sample, the object plane of the optical system being located at a known distance from the reference point along an axis parallel to the optical axis of the optical system, and the particle of interest being located outside of the object plane; using the reference image, digitally constructing a series of reconstructed
(Continued)

images, each associated with a predetermined offset of the object plane along the optical axis of the optical system; and using the series of reconstructed images, determining the distance along an axis parallel to the optical axis of the optical system, between the particle of interest and the reference point.

17 Claims, 4 Drawing Sheets

(51) Int. Cl.
| | |
|---|---|
| *G06T 7/00* | (2017.01) |
| *G01N 21/45* | (2006.01) |
| *G03H 1/00* | (2006.01) |
| *G03H 1/08* | (2006.01) |
| *G03H 1/04* | (2006.01) |
| *G01N 21/47* | (2006.01) |
| *G01N 15/14* | (2006.01) |
| *G01N 15/00* | (2006.01) |
| *G01N 15/10* | (2006.01) |

(52) U.S. Cl.
CPC ....... *G01N 21/4788* (2013.01); *G03H 1/0005* (2013.01); *G03H 1/041* (2013.01); *G03H 1/0443* (2013.01); *G03H 1/0866* (2013.01); *G06T 7/97* (2017.01); *G06T 15/10* (2013.01); *G01N 15/1463* (2013.01); *G01N 15/1475* (2013.01); *G01N 2015/0065* (2013.01); *G01N 2015/1006* (2013.01); *G01N 2015/1445* (2013.01); *G01N 2015/1452* (2013.01); *G01N 2015/1454* (2013.01); *G03H 2001/005* (2013.01); *G03H 2001/0033* (2013.01); *G03H 2001/0428* (2013.01); *G03H 2001/0447* (2013.01); *G03H 2001/0452* (2013.01); *G03H 2001/0467* (2013.01); *G03H 2001/0883* (2013.01)

(56) References Cited

U.S. PATENT DOCUMENTS

| | | | | |
|---|---|---|---|---|
| 2013/0084598 | A1* | 4/2013 | Moy | C12Q 1/04 435/34 |
| 2017/0284926 | A1* | 10/2017 | Perraut | G01N 15/1475 |
| 2017/0336326 | A1* | 11/2017 | Sirat | G02B 21/0056 |
| 2017/0363533 | A1* | 12/2017 | Perraut | G01N 15/1434 |
| 2018/0074305 | A1* | 3/2018 | Atzler | G01N 21/6458 |

OTHER PUBLICATIONS

Willert, C. E., and M. Gharib. "Three-dimensional particle imaging with a single camera." Experiments in Fluids 12.6 (1992): 353-358. (Year: 1992).*

Sheng, Jian, Edwin Malkiel, and Joseph Katz. "Digital holographic microscope for measuring three-dimensional particle distributions and motions." Applied optics 45.16 (2006): 3893-3901. (Year: 2006).*

Xu, Lei, et al. "Imaging analysis of digital holography." Optics Express 13.7 (2005): 2444-2452. (Year: 2005).*

International Search Report dated Feb. 11, 2016, in PCT/EP2015/076530, filed Nov. 13, 2015.

French Search Report dated Aug. 19, 2015, in French patent Application No. 1460947, filed Nov. 13, 2014.

Choi et al., "Three-dimensional volumetric measurement of red blood cell motion using digital holographic microscopy", Applied Optics, vol. 48, No. 16, Jun. 1, 2009, p. 2983-2990, XP 1524402A.

Pan et al., "Digital holography of particle fields: reconstruction by use of complex amplitude", Applied Optics, vol. 42, No. 5, Feb. 10, 2003, p. 827-833, XP 1160042A.

Pavillon et al., "Cell Optical Density and Molecular Composition Revealed by Simultaneous Multimodal Label-Free Imaging", Biophysical Journal, vol. 105, Sep. 2013, p. 1123-1132, XP 28712247A.

Xu et al., "Digital in-line holography of microspheres", Applied Optics, vol. 41, No. 25, Sep. 1, 2002, p. 5367-5375, XP 55086866A.

Fugal et al., "Practical methods for automated reconstruction and characterization of particles in digital in-line holograms", Measurement Science and Technology, vol. 20, No. 7, May 21, 2009, p. 1-14, XP 20160483A.

Lee et al., "Holographic microscopy of holographically trapped three-dimensional structures", Optics Express, vol. 15, No. 4, Feb. 19, 2007, p. 1505-1512.

Wilson et al., "3D Localization of weak scatterers in digital holographic microscopy using Rayleigh-Sommerfeld back-propagation", Optics Express, vol. 20, No. 15, Jul. 16, 2012, p. 16735-16744.

* cited by examiner

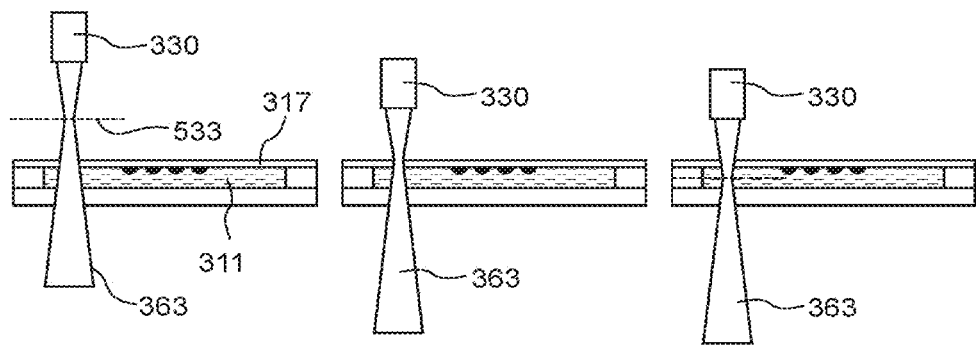
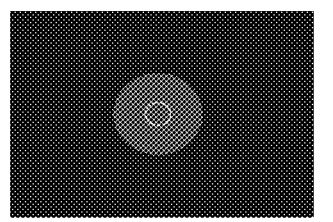
FIG.5A
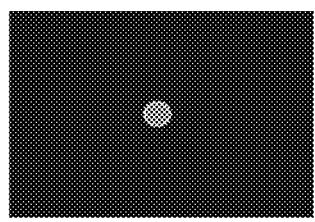
FIG.5B
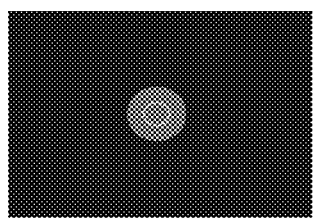
FIG.5C
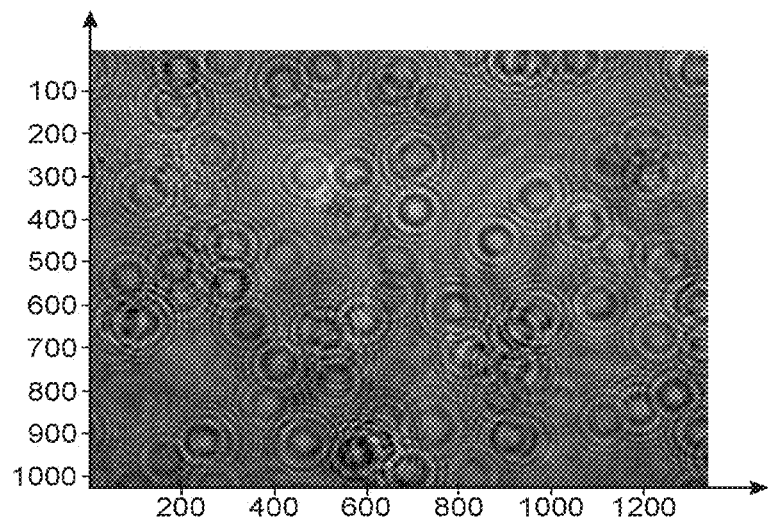
FIG.6

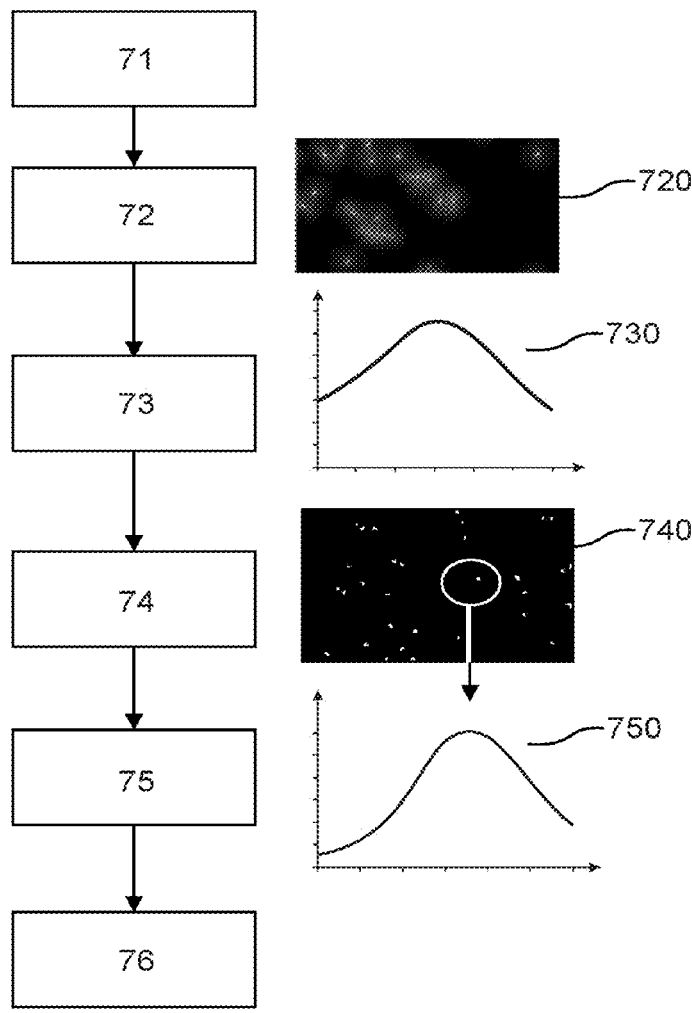
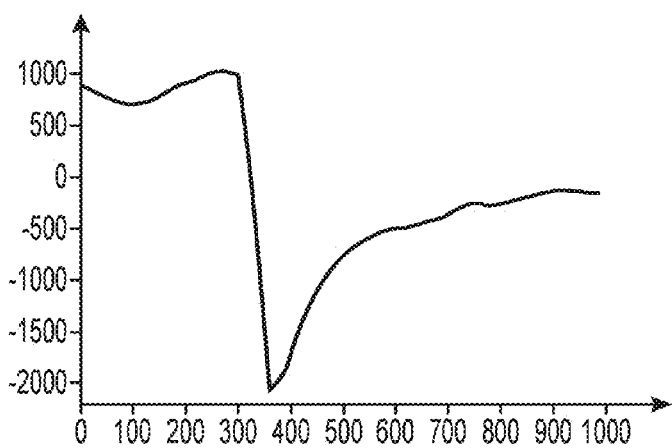
FIG.8

ANALYSIS METHOD INCLUDING THE DETERMINATION OF A POSITION OF A BIOLOGICAL PARTICLE

TECHNICAL FIELD

This invention relates to the field of analysing a sample receiving biological particles, with this analysis consisting in particular in determining a position of at least one of said biological particles, along an axis of the depth of the sample.

PRIOR ART

Many cases are known in prior art wherein it is necessary to know the position of a biological particle, along the axis of the depth of the sample receiving this particle.

A commonly used solution consists in acquiring a series of images of the sample, at different depths in the latter. The image wherein a clear image of the biological particle is observed is then sought.

A disadvantage of this solution it that it does not make it possible to know the position of a transparent biological particle of which the clear image is confounded with the image of the surrounding environment.

An objective of this invention is to propose a method and a device that do not have this disadvantage.

In particular, an objective of this invention is to propose a method and a device making it possible to determine the position of any biological particle, according to at least one axis of the space in three dimensions.

DISCLOSURE OF THE INVENTION

This objective is achieved with a method of analysis of a sample receiving biological particles, among which a particle of interest, with the method being implemented in a device comprising the sample arranged between a first light source and an optical system, said method comprising the following steps:

defining a reference point, located on a first interface of the sample or at a known distance from the latter along an axis parallel to the optical axis of the optical system;

using the first light source, illuminating a region receiving the particle of interest, referred to as illuminated region;

using a sensor located in an image plane of the optical system, acquisition of an image of the illuminated region, referred to as reference image, the particle of interest being located outside of the object plane of the optical system, and the distance, along an axis parallel to the optical axis of the optical system, between said object plane and the reference point, being a known distance referred to as useful distance;

using the reference image, digital construction of a series of reconstructed images, each of which is associated with a predetermined offset of the object plane along the optical axis of said optical system;

using the series of reconstructed images, determining the distance along an axis parallel to the optical axis of the optical system, between the particle of interest and said object plane.

The invention therefore advantageously comprises a step of detecting the reference point, by a placing of the optical system in such a way that its object plane is placed on the reference point, on said first interface or at the known distance from the latter, and arrangement of the optical system in such a way that the particle of interest is located outside of the object plane of the optical system.

The reference image is acquired for this arrangement of the optical system, such that the particle of interest is located outside of the object plane of the optical system.

This arrangement of the optical system can correspond directly to the arrangement of the optical system implemented in order to detect the reference point. In this case, the reference image, or defocused image, is acquired directly after detection of the reference point.

Alternatively, after detection of the reference point, the method comprises a step of offsetting the object plane of the optical system relatively to said reference point, by a translation of a support receiving the sample relatively to the optical system. The reference image, or defocused image, is acquired after this step of offsetting.

The invention makes it possible to know with precision a distance between the object plane and said reference point. It is as such possible to know with precision a distance between the particle of interest and the object plane, which then makes it possible to best position a device for analysis in order to study the particle of interest.

Advantageously, the method comprises a determining of the distance between the particle of interest and said reference point, using said distance between the particle of interest and said object plane as well as said useful distance.

It can furthermore comprise a determining of the presence of said particle of interest in the medium starting from the distance between said particle of interest and said object plane.

Determining of the useful distance comprises the following sub-steps:

illuminating the reference point by a laser beam, said laser beam being focused by said optical system;

acquiring an image on the sensor representing the reflection of the laser beam on an interface of the sample;

adjusting the useful distance along an axis parallel to the optical axis of the optical system, between the sample and the optical system, according to the intensity of the image formed on the sensor.

Typically, the biological particles adhere to a second interface of the sample, with the first and second interfaces being separate or confounded.

The distance along an axis parallel to the optical axis of the optical system, between the position of the object plane associated with the reference image, and the projection of the reference point according to this axis and on the second interface, is for example between +5 µm and +2000 µm or between −5 µm and −2000 µm.

The illuminated region can comprise a plurality of biological particles.

The first light source typically has a spectral width less than 200 nm.

Advantageously, the method further comprises a determining, using said series of reconstructed images, of the position of the particle of interest in a plane orthogonal to the optical axis of the optical system.

Each reconstructed image is formed by a real part and an imaginary part, and among the real and imaginary parts, only the imaginary parts of the reconstructed images are advantageously used to determine the distance along an axis parallel to the optical axis of the optical system, between the particle of interest and the reference point.

Each reconstructed image can be associated with an offset along the optical axis of the optical system and with a value of a useful parameter, in such a way as to constitute a function that describes the change in the useful parameter according to said offset, the determining of the distance between the particle and the object plane implementing a search for a remarkable value, in particular an extremum, an inflection point or a passage through zero of said function.

The determining of the distance between the particle of interest and the object plane advantageously comprises the following sub-steps:

using a first series of reconstructed images associated with a first step of offsets of the object plane, determining an approximated distance between the particle of interest and said object plane;

using a second series of reconstructed images associated with a second step of offsets of the object plane, with the second step being finer than the first step, determining a precise distance between the particle of interest and said object plane.

Using the distance between the particle of interest and said object plane, the optical system is advantageously displaced in relation to said particle of interest in such a way as to focus the analysis laser beam (363) on the particle of interest.

Using said distance between the particle of interest and said object plane, the optical system is advantageously displaced in relation to said particle of interest in such a way as to adjust the focusing of a photodetector located in the plan image.

The method can furthermore include a step of counting the number of biological particles present in the sample. These biological particles can include bacteria, spores, cells, yeasts or micro-organisms.

The invention also relates to a device for analysing a sample receiving biological particles, among which a particle of interest, with the device comprising:

a first light source;

an imaging unit comprising an optical system and a sensor, such that the sensor is located in an image plane of the optical system, said image plane being the conjugate, by the optical system, of an object plane;

a support adapted to receive the sample, arranged between the first light source and the imaging unit;

means for translation, adapted to displace the support relatively to the imaging means, along an axis parallel to the optical axis of the optical system; and calculation means:

connected to a memory storing information relative to a reference point located on a first interface of the sample or at a known distance from the latter along the optical axis of the optical system, receiving as input an image acquired by the sensor, referred to as reference image when said object plane is offset with respect to said reference point adapted to carry out, using the reference image, a digital construction of a series of reconstructed images, each of which is associated with a predetermined offset of the object plane along the optical axis of the optical system; and supplying as output the distance along an axis parallel to the optical axis of the optical system, between the particle of interest and the object plane.

The device can also comprise a laser, adapted to provide a laser beam aligned with the optical axis of the optical system, and coupled to the optical system in such a way that the focusing point of the laser beam corresponds to the object plane.

BRIEF DESCRIPTION OF THE DRAWINGS

This invention shall be better understood when reading the description of embodiments provided solely for the purposes of information and in no way limiting, in reference to the annexed drawings wherein:

FIGS. 5A to 5C show a detail of the method shown in FIG. 4;

FIG. 6 shows a reference image according to the invention;

FIG. 7 diagrammatically shows a detail of a third embodiment of a method for analysis according to the invention; and FIG. 8 shows a profile used in a fourth embodiment of the method according to the invention.

DETAILED DESCRIPTION OF PARTICULAR EMBODIMENTS

The method for analysis and the device for analysis according to the invention will be described jointly, with the device for analysis according to the invention being adapted to the implementing of the method of analysis according to the invention.

Figure 1:
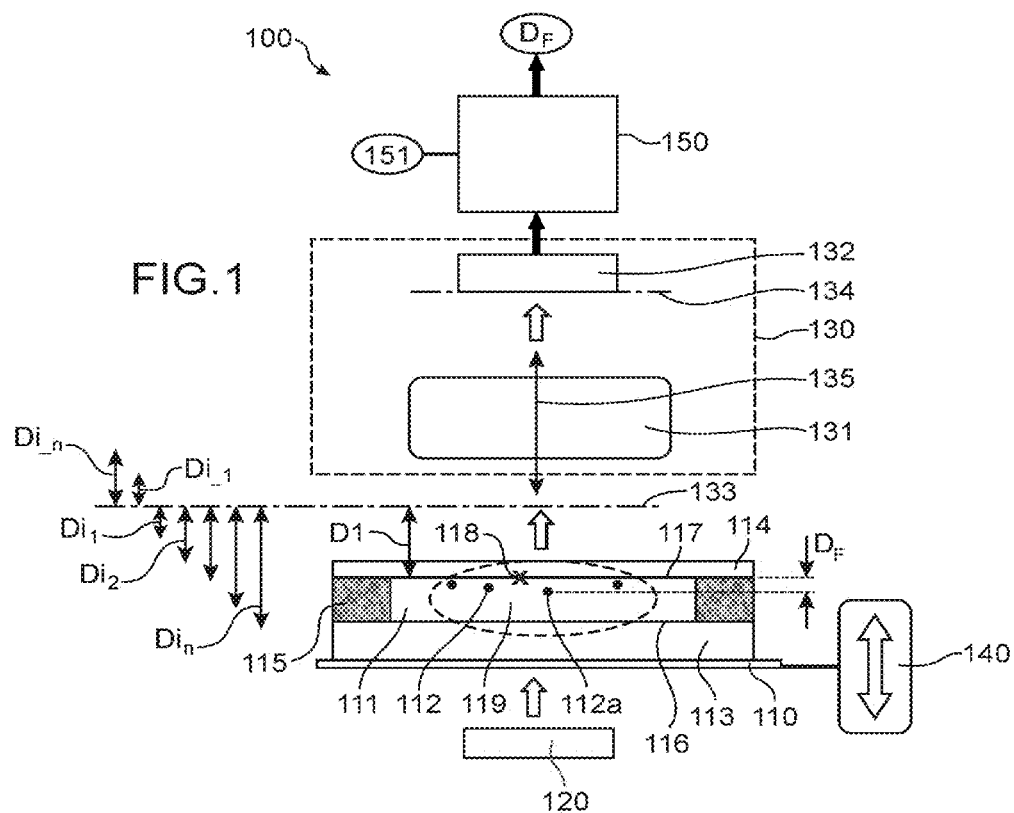
FIG. 1 shows a first embodiment of a device for analysis according to the invention.
Figure 2:
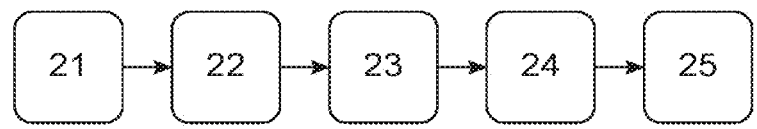
FIG. 2 diagrammatically shows a first embodiment of a method for analysis according to the invention.

FIG. 1 shows a first embodiment of a device for analysis 100 according to the invention. FIG. 2 shows a first embodiment of a method for analysis according to the invention, implemented in the device for analysis 100.

The device for analysis 100 comprises a support 110, adapted to receive a sample 111.

The support 110 is for example a clamp, or a transparent plate, or a plate pierced with an opening in order to allow light rays to pass through.

The sample 111 is a transparent or translucent medium, i.e. having a coefficient of transmission greater than or equal to 70% in the visible spectrum or more generally in a spectrum between 300 nm and 1000 nm.

The sample 111 is defined by interfaces, or boundaries, or limits between the sample and a medium located in direct contact with it.

The sample consists of a liquid such as water, a buffer solution, a liquid containing a reagent, a culture medium, and biological particles 112 located in this liquid. Alternatively, the sample consists of a solid medium such as an agar, and biological particles located on this solid medium. According to another alternative, the sample consists of a gas wherein biological particles are located. As such, the biological particles can be located inside the sample (for example be in a liquid), or be flush on the surface of the sample (for example be located on an agar).

The biological particles 112 designate for example bacteria, spores, cells, yeasts, or any type of micro-organism. One of these biological particles is named particle of interest 112A.

In the example shown in FIG. 1, the sample 111 comprises a culture medium enclosed within a fluidic chamber defined by a lower slide 113, for example a standard microscope slide, an upper slide 114, and an adhesive 115 laterally surrounding the sample 111 and connecting together the upper and lower slides. The upper and lower slides 113, 114 are transparent in the visible range and where applicable in other useful wavelengths.

The boundary between the sample and the lower slide 113 defines a lower interface 116 of the sample 111. The boundary between the upper slide 114 and the sample defines an upper interface 117 of the sample 111.

A first light source 120 is located upstream of the sample 111, in the direction of propagation of the light, from the first light source to the sample 111. In what follows, the terms upstream and downstream refer to the direction of propagation of the light, from the first light source 120 to the sample 111.

The first light source 120 is for example a laser, a light-emitting diode, a white lamp in particular a mercury vapour lamp whether or not filtered. The first light source can comprise an optical fibre in order to convey the light under the lower blade 113.

The first light source 120 is advantageously time coherent. It has a spectral width advantageously less than 200 nm, even less than 100 nm or even 25 nm.

Preferably, the first light source 120 is space coherent.

More details will be provided in what follows on the time and space coherency of the first light source 120.

The first light source illuminates in transmission a region 119 of the sample. The particle of interest 112A is located in the region 119.

An imaging unit 130 is located downstream of the upper slide 114, in the direction of propagation of the light, from the first light source to the sample 111. In the embodiment described, the imaging unit 130 is located above the sample 111.

The imaging unit 130 comprises an optical system 131 and a sensor 132.

The optical system 131 consists for example of an objective, in particular a microscope objective. It has an object plane 133 and an image plane 134. The image plane 134 is the conjugate (or image) of the object plane by the optical system. In other terms, an object located in the object plane corresponds to a clear image in the image plane.

The sensor 132 is for example a matrix sensor of the CCD or CMOS type. It is located in the image plane 134. As such, the sensor 132 acquires an image in transmission, of a portion of the object plane 133.

In an infinite plane configuration, the object plane is the object focal plane of the optical system, and the image plane is sent to infinity. A proximity optical device, for example a tube lens, makes it possible to focus the image plane on the sensor 132. In the rest of the text, the term sensor 132 groups together the sensor 132 and its proximity optical device.

The optical system 131 has an optical axis 135. The optical axis is orthogonal to the object plane and to the image plane. The optical axis 135 defines the depth of the sample 111. This axis connects the lower and upper interfaces 116, 117 of the sample 111. Preferably, the optical axis 135 is substantially orthogonal to the lower and upper interfaces 116, 117. The term interface designates a boundary of the studied sample 111.

The analysis in terms of the invention comprises in particular a determining of the position of the particle of interest 112A along an axis parallel to the optical axis 135.

The device 100 further comprises means for translation 140, adapted to displace the imaging unit 130 along an axis parallel to the optical axis 135. In an infinite plane configuration such as defined hereinabove, the means of translation 140 can only displace the optical system 131, with the sensor 132 remaining fixed. Alternatively, the means of translation 140 are adapted to displace the support 110 along an axis parallel to the optical axis 135.

According to an embodiment, the means of translation 140 furthermore carry out translations according to two other axes defining a plane orthogonal to the optical axis 135.

The sensor 132 is connected to the means for calculating 150, in particular a processor or a microprocessor.

The device 100 is adapted to implementing the method according to the invention, shown diagrammatically in FIG. 2.

The method comprises a first step 21, of determining a reference point 118. This step consists in selecting, or defining the reference point 118. This selection is generally arbitrary.

The reference point is located on a first interface of the sample 111, or at a known distance from this first interface, with this distance being defined along the optical axis 135.

In particular, the reference point is located on the upper interface 117 or lower interface 116. In the example shown in FIG. 1, the reference point is located on the upper interface 117 of the sample.

According to an alternative not shown, the reference point is not located directly on an interface of the sample, but at a known distance from the latter. For example, the reference point is located on a face of the upper slide 114 opposite the sample, with the thickness of the upper slide 114 being known.

In the device 100, the means for calculating 150 are connected to a memory 151 storing information relative to the reference point, in particular the distance along an axis parallel to the optical axis 135, between this reference point and said first interface and optionally its coordinates in a plane orthogonal to the optical axis 135.

The sample 111 is then illuminated using the first light source 120, as such forming in the sample an illuminated region 119 such as described hereinabove (step 22).

Then, an image in transmission of the illuminated region 119 is acquired, using the imaging unit 130 (step 23). This image is named reference image. During this acquisition, the object plane 133 is located at a known distance D1 from the point of interest 118, with this distance being defined along an axis parallel to the optical axis 135. The particle of interest 112A is located outside of the object plane 133. Preferably, during the acquisition of the reference image, the object plane is located outside of the sample 111. For example, when the reference point 118 is located on the upper interface 117, the object plane is located between 5 µm and 1500 µm above or below (upstream or downstream) of the reference point, preferably between 5 µm and 1000 µm, even between 5 µm and 800 µm. Here again, the distance is defined along an axis parallel to the optical axis 135.

Generally, during the acquisition of the reference image, the object plane is located at a distance greater than 2 µm, and preferably greater than 5 µm, preferably in the range [5 µm-1500 µm], even [5 µm-1000 µm], even [5 µm-800 µm] from an interface defining the sample 111. Alternatively, information is available a priori as to the position of a particle. The object plane is then offset, in relation to this a priori, by a value such as defined hereinabove.

In the embodiment shown in FIG. 1, an example of information a priori is the observation of biological particles adhering to a surface, for example the upper slide 114 delimiting the sample 111. Knowledge of the position of the slide makes it possible to establish an a priori on the position of the particles, the latter adhering to the face 117 of this slide adjacent to the sample.

It is said that the reference image is the image of a portion of the illuminated region, because it is formed by light rays coming from this illuminated region. The reference image is in particular a hologram, formed by the interference of light rays coming from the first light source and scattered by a biological particle of the sample, with light rays coming from the first light source 120 and having passed through the sample without being scattered. The reference image comprises in particular a hologram associated with the particle of interest.

In the device 100, the calculation means 150 are connected to the sensor 132 in order to receive the reference image.

In a step 24, a digital construction of a series of reconstructed images is implemented. Each reconstructed image corresponds to a predetermined offset, along the optical axis 135, of the object plane relatively to the position of the object plane associated with the reference image. These are virtual offsets, i.e. simulated by the digital construction, not physically implemented. In other terms, each reconstructed image is calculated in a reconstruction plane, associated with a predetermined offset with respect to the object plane. More precisely, each reconstruction plane corresponds to the image, by the optical system, of an object plane, offset with respect to the object plane by this predetermined offset. This is generally referred to as digital propagation. These offsets are noted as $Di_1, Di_2, \ldots Di_n, Di_{-1}, \ldots Di_{-n}$. Preferably, the offsets extend between two end positions with respect to the object plane, with these two end positions surrounding the upper interface 117 and, more generally, the point of interest. These offsets can be distributed according to a regular step, in particular a step between 0.10 µm and 1 µm, for example 0.25 µm or 0.20 µm. As such, the images that would be acquired by the sensor 132, if the object plane were successively at the distances $Di_1, Di_2, \ldots Di_n, Di_{-1}, \ldots Di_{-n}$ from the position of the object plane associated with the reference image, are digitally reconstructed. The reference image is an image acquired experimentally, while the reconstructed images form images constructed by digital propagation.

The difference between the two end positions associated with these offsets depends on the sample 111 observed, and in particular on its thickness. When there is no a priori as to the position of the particles of interest, the two end positions are determined in such a way that they are located on either side of the sample 111. When there is an a priori on the position of a particle of interest in the sample, the two end positions are established in order to be arranged on either side of this position.

The digital reconstruction uses the Fourier transform of the reference image (having possible been subjected to a prior treatment), to which is applied a propagation operator before switching it back in the real space. The propagation operator is a function of the offset associated with the reconstructed image calculated.

According to the invention, the propagation operator is for example an integral based on the Rayleigh Sommerfeld equation.

In the article "*3D Localization of weak scatterers in digital holographic microscopy using Rayleigh-Sommerfeld back-propagation*", 16 Jul. 2012/Vol. 20, No 15/OPTICS EXPRESS, 16735-16744, Wilson et al. describes an example of a digital propagation implemented using the image of a microsphere. Another example of digital propagation is described by Lee et al. in the article "*Holographic microscopy of holographically trapped three-dimensional structures*", 19 Feb. 2007/Vol. 15, No. 4/OPTICS EXPRESS 1505-1512.

The reconstructed images are complex images, i.e. with a real part and an imaginary part. They include a set of points, with each point of the image being assigned a complex magnitude.

The calculation means 150 of the device 100 according to the invention are adapted to carry out, using the reference image, a digital construction of a series of reconstructed images, such as described hereinabove.

Using the series of reconstructed images, the distance between the particle of interest 112A and the reference point 118 is then determined, with this distance being defined according to an axis parallel to the axis 135 (step 25). Alternatively, this is limited, using the series of reconstructed images, to the distance $D_{ref}$ between the particle of interest 112A and the object plane 133.

For this, the distance $D_{ref}$ is calculated along the optical axis 135, between the particle of interest 112A, and the object plane associated with the reference image. Knowing the distance $D_1$ along the optical axis 135 between this object plane and the reference point 118, it is deduced from this the distance $D_F$ between the particle of interest 112A and the reference point 118 along the optical axis 135.

In order to determine the distance $D_{ref}$ along the optical axis 135, between the particle of interest 112A, and the object plane associated with the reference image, each reconstructed image is associated with a value of a useful parameter, with the useful parameter being a function of a complex intensity parameter (or complex amplitude) of the points belonging to the reconstructed images. A complex intensity parameter (or complex amplitude) of a reconstructed image is for example the imaginary part, the real part, the modulus or the phase of the reconstructed image. Preferably, these values of the useful parameter are gathered together in the form of a profile, representing the value of the useful parameter according to the offset of each reconstructed image, along the optical axis 135, with respect to the object plane 133.

Then, a remarkable value on this profile is sought, for example a maximum or an inflection point or a passage through zero. This remarkable value is associated with the offset along the optical axis 135, between the particle of interest and the position of the object plane 133 associated with the reference image. Preferably, it is arranged that the remarkable value to be searched for is a maximum and generally an extremum, in order to limit the effect of uncertainty during the passage by a second derivative (detection of an inflection point), and in order to overcome a correction of the measurement bias (detection of a passing through zero). But the remarkable value of the useful parameter can also be a passing through zero of the function that describes the change of this parameter according to the offset between the reconstructed image and the object plane 133, or an inflection point of this function, or any other criterion.

As such, generally, the distance $D_{ref}$ is determined between the object plane 133 of the reference image and a particle of interest 112A, by the succession of the following steps:

identifying, on the reference image, of a hologram associated with said particle of interest, digital reconstruction of images, by applying a projection operator to said reference image, or to a region of interest of the reference image comprising said hologram, in such a way as to obtain, for a plurality of predetermined offsets $Di_1, Di_2, \ldots Di_n, Di_{-1}, \ldots Di_{-n}$ with respect to the object plane 133, a reconstructed image, each reconstructed image corresponding to each offset, extracting, in each reconstructed image, a parameter that represents the complex value of each point of the image, referred to as useful parameter, analysing the change in this useful parameter according to said offset and identifying a remarkable value of this useful parameter, determining of the offset corresponding to said remarkable value of this useful parameter, with the distance $D_{ref}$ between the particle of interest 112A and the object plane 133 then being considered to be equal to this offset.

Knowing the distance $D_1$ between the object plane 133 and the reference point 118, it is then possible to deduce the distance $D_F$ between the particle of interest 112A and the reference point 118, by the operation $D_F=D_{ref}-D_1$ By extraction, on each reconstructed image, of a useful parameter, this means the calculation of a parameter that represents the various points constituting the image, for example by taking a sum or an average of the complex magnitudes associated with each one of these points.

The useful parameter can be the square of the imaginary portion of the image, determined using the value of the imaginary portion of the various points constituting the image. The useful parameter then corresponds to the average of the square of the imaginary portion of all of the points constituting the image. The inventors have observed that such a parameter makes it possible to obtain good locating precision.

Besides the imaging part, the parameter can also include the value of the real part of the points constituting the image, or their modulus, or the square of these various magnitudes. The inventors have shown that it is possible to locate the position, along the optical axis 135, of a particle of interest 112A, with this position corresponding to a remarkable value of the useful parameter, and for example:

a maximum: this is the case when a change is observed, along the optical axis 135, in the square of the imaginary part, or in the modules, or in the square of the modulus of the image.

a passing through zero, for example when a change is observed, along the optical axis 135, in the real part of the image or of its square.

Alternatively or in a complementary manner, the identification of a remarkable value of said parameter of interest makes it possible to conclude as to the presence of a particle of interest 112A in the medium, in the offset range considered, with the distance between the particle of interest 112A and the object plane $D_{ref}$ not being necessarily memorised.

To each particle of interest 112A corresponds a hologram on the reference image. It is then possible to select a region of interest being limited to a hologram, and to apply the steps described hereinabove to each region of interest associated with a hologram.

The calculation means 150 provide as output the distance $D_F$, along the axis 135, between the particle of interest 112A and the reference point 118.

The recourse to a digital propagation makes it possible to reduce the number of images of the sample to be acquired. In particular, the acquisition of a single image is sufficient. The method according to the invention is therefore particularly fast and can be automated.

In certain cases, when the particle of interest is located in the object plane of the optical system, its image cannot be distinguished from the image of the surrounding medium (with the surrounding medium corresponding to the portion of sample 111 surrounding the particle of interest). This is for example the case when the particle of interest is in a medium with the same coefficient of transmission or close refractive index (for example within 20%), in the spectrum of the first light source. In this case, the method according to prior art such as described in the introduction does not make it possible to determine the position of the particle of interest. On the other hand, the particle of interest can be identified in a reconstructed image according to the invention, because this reconstructed image is a complex image that contains more information than an acquired image. As such, the method according to the invention makes it possible to determine the position of a particle along an axis parallel to the optical axis of the optical system, even when the particle cannot be distinguished from its surrounding medium in an image acquired when the particle is located in the object plane of the optical system.

Finally, the method according to the invention makes it possible to associate an image and a position of the object plane along the optical axis 135, with this position being determined with great precision (linked to the step of the offsets implemented in step 23). Such a precision would not be easy to achieve using physical and non-virtual offsets.

The reference image can include the hologram of a single biological particle, which then defines the particle of interest according to the invention.

Alternatively, the reference image comprises the hologram of several biological particles, one of these holograms is chosen arbitrarily in order to define the particle of interest according to the invention, and portions of the reconstructed images, or regions of interest, are used centred on one of these holograms.

It is possible to implement a preliminary step for the standardisation of the reference image. For this, a so-called background image is acquired, that represents the defects of the optical system (internal reflections, dust, etc.). The background image corresponds for example to the image acquired by displacing the sample in a plane parallel to the object plane, while an image is being taken. Alternatively, the background image is an average image formed using several static images obtained for several positions of the sample in a plane parallel to the object plane. Then, the reference image is divided by the background image, pixel by pixel. A standardised reference image is as such obtained. Such a standardisation improves the results of the method.

According to a first alternative of the invention, the digital propagation is carried out using the reference image used directly, or using the standardised reference image such as defined hereinabove.

The reconstructed image associated with an offset z is noted as:

$$U_p(z)=TF^{-1}\{TF(U_0) \times H(z)\}$$

with $U_0$ the image used to carry out the digital propagation (here the reference image or the standardised reference image), TF the Fourier transform operator, $TF^{-1}$ the inverse Fourier transform, X the multiplication term by term of matrices, and H a propagation operator based on the Rayleigh Sommerfeld integral.

In the example shown here, we have in particular:

$$H(u,v,z)=\exp[-|z|*Im(p(u,v))+i*z*Re(p(u,v))]$$

with

Re the real part operator, Im the imaginary part operator, $i^2=-1$, u and v the coordinates in the Fourier space, associated with the coordinates x, y a plane orthogonal to the axis 135, in the real space, $$p(u, v) = k \times \Delta_p \times (\sqrt{1 - u^2 - v^2} - 1), \text{ and } k = \frac{2\pi}{\lambda}.$$

The coordinates u and v are defined in the following way:

$$u = \frac{\lambda}{\Delta_p}\left(\frac{0}{N_x} - \frac{1}{2}\right); \frac{\lambda}{\Delta_p}\left(\frac{1}{N_x} - \frac{1}{2}\right); \ldots ; \frac{\lambda}{\Delta_p}\left(\frac{N_x - 1}{N_x} - \frac{1}{2}\right)$$

by a step of $$\frac{\lambda}{N_x \times \Delta_p}$$

$$v = \frac{\lambda}{\Delta_p}\left(\frac{0}{N_y} - \frac{1}{2}\right); \frac{\lambda}{\Delta_p}\left(\frac{1}{N_y} - \frac{1}{2}\right); \ldots ; \frac{\lambda}{\Delta_p}\left(\frac{N_y - 1}{N_y} - \frac{1}{2}\right)$$

by a step of $$\frac{\lambda}{N_y \times \Delta_p}$$

and with $\Delta_p$ the size of the sampling step, defined in the object plane (therefore linked to the pixel pitch of the sensor 132 and to the magnification factor of the optical system 131), $N_x$ and $N_y$, the numbers of pixels according to x, respectively y, in the image $U_0$, $\lambda$ the central wavelength of the first light source.

The position of the particle of interest along the optical axis of the optical system is then determined, using the imaginary part of each reconstructed image $U_p(z)$. In particular, the reconstructed image or a portion of the reconstructed image is sought, of which the square of the imaginary part (i.e. the average value of the square of the imaginary part of the various points constituting the image) is maximum. A portion of the reconstructed image is a part of the reconstructed image, centred on the image of the particle of interest. If the reference image relates to several biological particles, the same reference image can be used to determine the position of each one of these biological particles, by using each time reconstructed images centred on a different biological particle.

Figure 3:
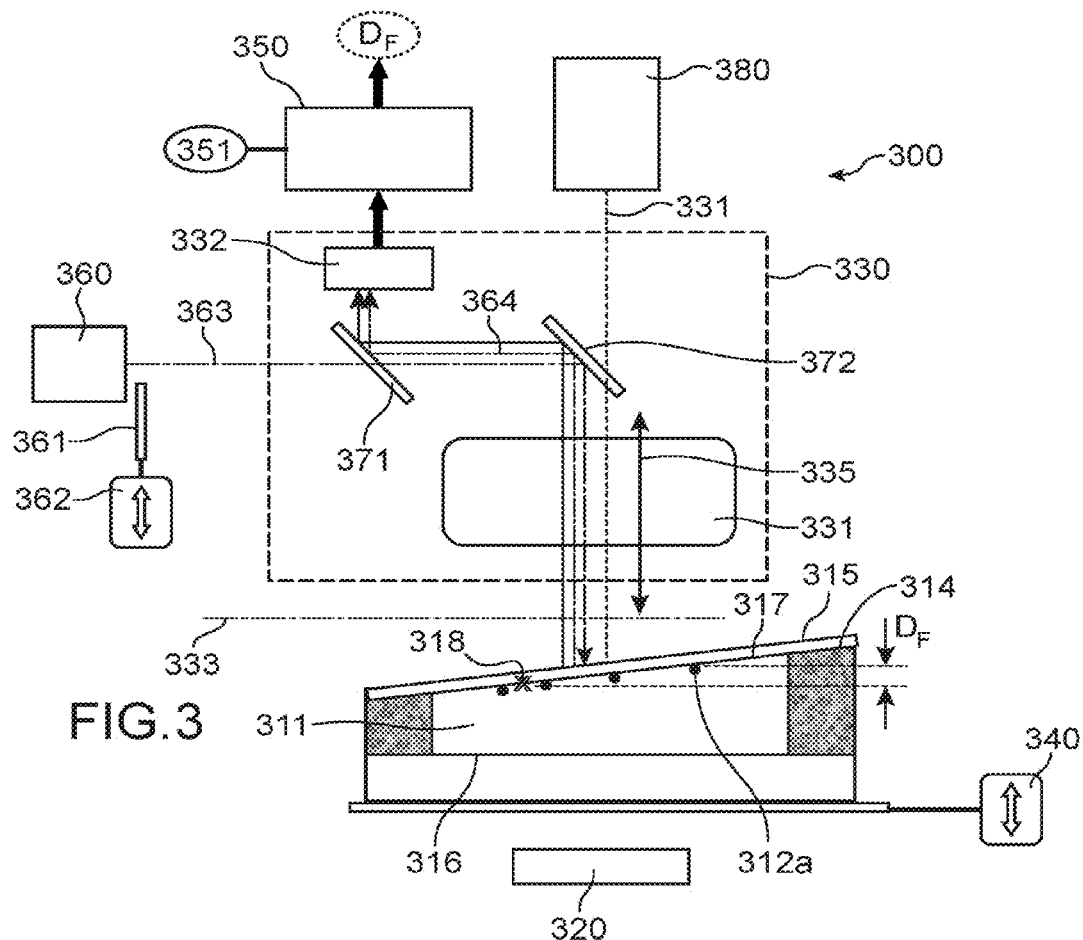
FIG. 3 shows a second embodiment of a device for analysis according to the invention.

In reference to FIGS. 3 and 4, a second embodiment of the method and of the device 300 according to the invention shall now be described. FIG. 3 will be described only for its differences in relation to FIG. 1.

The numerical references 111, 120, 112A, 116, 117, 118, 130, 131, 132, 135, 120, 150, 151 of FIG. 1 correspond respectively to the numerical references 311, 320, 312A, 316, 317, 318, 330, 331, 332, 335, 320, 350, 351 of FIG. 3.

Each one of the characteristics that distinguishes the device according to FIG. 3 from the device according to FIG. 1 can be isolated and combined independently with the device of FIG. 1 in order to form many other alternatives of the invention.

According to an advantageous embodiment such as shown in FIG. 3, the biological particles adhere directly to a second interface of the sample.

The straight line parallel to the axis 335 and passing through the reference point 318 passes through this second interface.

This second interface is advantageously confounded with the first interface such as defined hereinabove. In the opposite case, the position of the first interface relatively to the second interface is preferably known, along an axis parallel to the optical axis 135. In particular, this position extending along an axis parallel to the optical axis 135 and passing through the reference point 318.

There is as such knowledge a priori on the position, along the optical axis 335, of the reference point 318 relatively to the biological particles.

The second interface is substantially orthogonal to the axis 335. This is in particular the lower or upper interface 316, 317 of the sample.

In practice, are studied for example:

an agar, the biological particles extending over the upper surface of the latter, or biological particles that adhere naturally on a slide covering the sample, said slide being located above the sample.

In the example shown in FIG. 3, the biological particles adhere to the upper interface 317.

The upper interface is slightly tilted relatively to the plane orthogonal to the axis 335, typically by an angle less than 0.1 rad, even 0.05 rad or 0.02 rad.

The method according to the invention makes it possible to overcome the uncertainty on the positioning of the biological particles along the axis 335, when the upper slide, defining the upper interface of the sample, is tilted relatively to a plane orthogonal to the axis 335.

More generally, the method according to the invention makes it possible to overcome the uncertainty on the positioning of the biological particles along the axis 335, when the upper slide, defining the upper interface of the sample, is deformed relatively to a plane orthogonal to the axis 335. This deformation can designate any deformation such as the biological particles adhering to said second interface be located inside a cylinder delimited by two planar surfaces perpendicular to the optical axis 335 and separated by at least 100 μm according to this axis, even less than 50 μm.

Preferably, the distance along an axis parallel to the optical axis 335, between the position of the object plane associated with the reference image, and the projection of the reference point 318 according to this axis and on the second interface, is between +5 μm and +1500 μm or between −5 μm and −1500 μm. Advantageously, this distance is between +5 μm and +1000 μm or −5 μm and −1000 μm, or even between +5 μm and +800 μm or −5 μm and −800 μm, or even between +5 μm and +200 μm or −5 μm and −200 μm. Optimal defocusing ranges are as such defined, offering easier calculation of the distance between the particle of interest and the reference point.

Since the biological particles adhere to said second interface and are located in a cylinder with limited height, it is easy to ensure during the acquisition of the reference image, that the particle of interest is located at a distance from the object plane located in an optimal defocusing range.

The width of the optimal defocusing ranges can depend on the characteristics of the first light source 320, in particular its time and space coherency.

As such, it is possible to adapt the first light source according to a distance along the optical axis 335, between several particles of interest that are sought to be studied, in such a way that these particles of interest are located simultaneously in an optimal defocusing range.

For example, a source of white light can be used, for an optimal defocusing range from +5 μm to +200 μm, and from −5 µm to −200 µm. The more the spectral width of the first light source is restricted, the more the width of the optimal defocusing range increases.

Furthermore, the smaller the apparent diameter of the first light source 320 is, the wider the optimal defocusing range is.

In the example shown in FIG. 3, the device for analysis 300 comprises means for determining the distance, along an axis parallel to the optical axis 335, between the reference point and the position of the object plane of the optical system associated with the reference image. This distance is named useful distance.

These means include in particular a laser 360, adapted to illuminate the reference point 318. A shutter 361 connected to a translation plate 362 makes it possible to close off the output of the laser, when it is not desired for the laser beam 363 to illuminate the reference point 318.

The laser beam 363 is advantageously incident on the reference point, along an axis parallel to the optical axis 335.

The laser beam 363 and the image sensor 332 are optically coupled to the same optical system 331, in such a way that the focusing point of the laser beam corresponds to the object plane of the sensor.

In the example shown in FIG. 3, the reference point is located on the upper interface 317, that is why the laser beam 363 penetrates into the sample via this upper interface 317.

The laser beam 363 passes through a first separating slide 371, then is reflected on a second separating slide 372, before reaching the upper interface 317. Each separating slide can be a dichroic slide. Alternatively, a cube or a semi-reflecting mirror is used.

Figure 4:
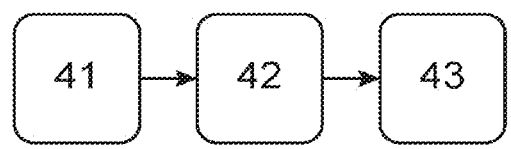
FIG. 4 diagrammatically shows a detail of a second embodiment of a method for analysis according to the invention.

The useful distance is determined by implementing the following sub-steps shown in FIG. 4.

In a sub-step 41, the reference point 318 is illuminated using the laser beam.

Then, the distance is adjusted, in particular along an axis parallel to the optical axis 335, between the sample, and the optical system 331, in such a way that the sensor 332 receives the image of a spot formed by the specular reflection of the laser beam 363 on the reference point (sub-step 42). This adjustment can be carried out thanks to the means of translation 340 described in reference to FIG. 1.

In practice, the definition of the reference point 318 can depend on the arbitrary position of the laser beam 363, in a plane orthogonal to the optical axis 335.

This adjustment implements detecting of the specular reflection of the laser beam 363 on the surface that receives the reference point. An example of such an adjustment is shown in FIGS. 5A to 5C, with the reference point being located on the upper interface 317.

The image 5A corresponds to a position of the object plane 533 above the upper interface 317. The image obtained on the sensor is a large spot that is not very bright.

The image 5B corresponds to a position of the object plane on the upper interface 317. The image obtained on the sensor is a narrow and very bright spot.

The image 5C corresponds to a position of the object plane below the upper interface 317. The image obtained on the sensor is a large spot that is not very bright.

By displacing the optical system along the axis 335, the following is observed successively:
  a large spot that is not very bright;
  a first narrow and very intense spot corresponding to the reflection of the laser beam 363 focused by the optical system 331 on the face 315 of the upper slide 314, opposite the sample, with this spot presenting a maximum intensity;
  a second narrow and intense spot corresponding to the reflection of the laser beam 363 focused by the optical system 331 on the face 317 of the upper slide 314, with this facing being adjacent to the sample, and thus constituting one of its interfaces, with this spot having a secondary maximum of the intensity, then
  a large spot that is not very bright, corresponding to the backscattering of the laser beam in the sample 311.

As such, the analysis of the change in the light intensity of the specular reflection signal of the laser beam, according to the relative separation between the optical system 331 and the sample 311 makes it possible to determine the position of the reference point 318, with the latter corresponding, in this example, to the focusing point of the laser beam with a surface able to reflect the beam, here the face 317 or the face 315.

In the example described hereinabove, the most intense image of the specular reflection and the image of the specular reflection having a secondary maximum of intensity, correspond to the configurations wherein the object plane passes through the intersection of the laser beam and, respectively, the face of the upper slide 314 opposite the sample, and the face of the upper slide 314 adjacent to the sample.

It can be noted that it is particularly interesting to detect the reflection of the laser beam on a face of the upper slide adjacent to the sample, as it will be visible even when the optical system is formed by an immersion objective.

Then, the method can include a sub-step 43, consisting in displacing by a known distance and along the optical axis 335, the support receiving the sample relatively to the means of imaging. Here again, the means of translation such as described in reference to FIG. 1 can be used. This sub-step can be useful for placing a particle of interest in an optimal defocusing range such as defined hereinabove.

FIG. 3 shows the laser beam 364 reflected on the upper interface 317, and imaged on the sensor by the optical system 331. The reflected laser beam 364 is reflected on the second separating slide 372, then on the first separating slide 371.

The calculation means 351 receive as input an image acquired by the sensor 351, when the shutter 361 is open, and the first light source 320 is extinguished. They control the means of translation 340 in order to implement the sub-step 42, and where applicable the sub-step 43.

Preferably, the method according to the invention also comprises a determining, using the series of reconstructed images, of the position of the particle of interest in a plane orthogonal to the optical axis of the optical system. An example of such a determination will be described further on in reference to FIG. 7.

The means for translation 340 can implement a translation according to two axes together defining a plane orthogonal to the optical axis 335. It is as such possible to successively locate several particles of interest of the same sample. After a single step of determining a reference point, the following series of steps such as described hereinabove are implemented several times:
  illuminating a region of the sample;
  acquiring a reference image;
  digital construction of a series of reconstructed images; and
  determining the distance between a particle of interest and the reference point, and/or detecting the number and the position using the reference image or one or several reconstructed images of particles of interest.

Between two series of these steps, the sample is translated in a plane orthogonal to the optical axis 335.

FIG. 3 also makes it possible to illustrate an additional step of analysis implemented in a method and a device according to the invention.

The device 300 comprises means for positioning the waist of the laser beam 363 (i.e. location of the laser beam of which the diameter is the narrowest) on the particle of interest.

The radiation emitted by the particle of interest, in reaction, is collected by the optical system 331 and received by a spectrometer 380 that analyses this radiation. The spectrometer 380 is for example a spectrometer that analyses on the Raman scattering or a fluorescence spectrometer. In this type of analysis, it is preferable that the excitation laser beam be centred on the particle examined. This prevents a disturbance of the Raman scattering spectrum in the vicinity of the particle.

The positioning of the waist of the laser beam 363 is implemented thanks to means for translation such as a translation plate (not shown), adapted to displace the sample relatively to the imaging means 331. These means of translation can be formed by the means of translation 340. The means of translation are controlled by the calculation means 350. The calculation means 350 use the position of the particle of interest relatively to the reference point to position the object plane of the optical system 331 on the particle of interest.

In particular, the imaging means are displaced in relation to the particle of interest in order to focus an analysis laser beam in a plane orthogonal to the optical axis of the imaging means, with this plane receiving said particle of interest, and the waist of the analysis laser beam is displaced in this plane in such a way as to place it exactly on the particle of interest.

Any other type of analysis that requires a precise positioning of the laser beam on the particle of interest can be considered. A laser source separate from the laser 360 can be used to analyse the particle of interest.

In the same way, a photodetector 332, optically coupled to the optical system 331, can be used, for example in order to collect a fluorescence signal emitted by the particle of interest 112A is response to an excitation signal. The knowledge of one of the distances mentioned hereinabove ($D_F$ or Dref) allows for the focusing of the optical system on the particle, which optimises the collection of the fluorescence signal by the photodetector 332.

In most cases, a medium comprises a plurality of particles of interest. During a first phase, the distance $D_{ref}$ or $D_F$ corresponding to each particle of interest 112A of the sample is determined and memorised. During the second phase, the relative positioning of the optical system 331 is adjusted in such a way that the object plane of this optical system comprises the particle of interest. This adjustment is carried out, successively, for each particle of interest, so as to optimise the analysis.

FIG. 6 shows an example of a reference image according to the invention. The axes of the abscissa and of the ordinates are graduated in pixels. Several diffraction patterns 61 are distinguished, each one associated with a biological particle.

A description shall now be given, in reference to FIG. 7, of a detailed example of the steps implemented in order to determine, using a first series of reconstructed images, the distance between the particle of interest and the reference point, along an axis parallel to the optical axis of the optical system.

In the example shown, we are in the embodiment such as described hereinabove, wherein we have:

$$H(u,v,z)=\exp[-|z|*Im(p(u,v))+i*z*Re(p(u,v))]$$

The following sub-steps are then implemented:

sub-step 71:

A calculation is made, for each reconstructed image of the first series of reconstructed images, of the square of the imaginary part. A first series of so-called useful reconstructed images is obtained. The square of the imaginary part of a reconstructed image therefore defines the intensity of the corresponding useful reconstructed image.

sub-step 72:

Each useful reconstructed image corresponds to the same matrix of pixels. According to the useful reconstructed image, the intensity associated with each pixel varies.

For each pixel, the maximum intensity is selected from the intensities on the various useful reconstructed images. The image of the maxima is as such formed.

Similarly, the image of the minima is formed.

An image of the gradients 720 is then calculated, corresponding to the difference between the image of the maxima and the image of the minima.

This step can be carried out using a first matrix, of which a dimension corresponds to the pixels, and the other dimension corresponds to the offset of the object plane associated with the useful reconstructed image. This offset is measured along the optical axis of the optical system, named axis (Oz) in what follows.

For example, if the useful reconstructed images each have X pixels in width and Y pixels in height, and N useful reconstructed images are reconstructed, the first matrix has XY columns and N lines.

The image of the minima then corresponds to a second matrix XY columns and 1 line. The image of the maxima corresponds to a third matrix XY columns and 1 line. The image of the gradients corresponds to a fourth matrix XY columns and 1 line, equal to the difference between the third and the second matrices.

sub-step 73:

The pixels that have a strong gradient of intensity along the axis (Oz) are selected. An average gradient associated with these pixels is defined. The position of the largest values of this average gradient roughly defines the position of the biological particles along the axis (Oz).

To do this, in the fourth matrix, the columns that have the highest values (for example first percentile) can be selected. A series of M pixels is as such defined. Then, these pixels in the first matrix are selected, and the selected pixels associated with the same offset along the axis (Oz) are combined (for example sum or average). A fifth matrix N lines and 1 column is as such formed.

The maximum is then searched for among the values of this fifth matrix, and the offset along the axis (Oz) is noted, associated with this maximum.

FIG. 730 shows the fifth matrix in the form of a profile wherein the axis of the abscissa is an offset along the axis (Oz), and the axis of the ordinates is the corresponding value on the fifth matrix.

The sub-step 73 defines an average position along the axis (Oz), of several biological particles imaged on the reference image. This average position defines an approximate position of a particle of interest according to the invention, by supposing that the biological particles are located substantially in the same plane orthogonal to the axis (Oz).

A gradient along the axis (Oz) associated with a selection of pixels that each have a strong gradient according to this axis is exploited. The maximum of the gradient associated with this selection is therefore all the more so easy to detect.

sub-step 74:

From the images of the first series of useful reconstructed images, the one associated with the position along the axis (Oz), calculated in the sub-step 73, is selected.

A thresholding is carried out on this image, in order to obtain a binary image 740. Then, the coordinates of the binary objects revealed by the thresholding are detected. An approximate position of each biological particle is as such calculated, in a plane orthogonal to the axis (Oz). This step can include a step of interpolation of each binary object by an ellipse, in order to further calculate an approximate geometrical shape for each binary object, and therefore for each biological particle.

The particle of interest is selected arbitrarily by arbitrarily selecting one of the binary objects. An approximate position of the particle of interest has therefore been determined, in a plane orthogonal to the axis (Oz).

On the binary image 740 is defined a region of interest comprising this single binary object. The region of interest is defined by positions of pixels. The region of interest is for example a square of 16*16 pixels.

sub-step 75:

This step is implemented using the first series of useful reconstructed images, by selecting in each useful reconstructed image a region corresponding to the region of interest such as defined hereinabove.

Alternatively, this step is implemented using a second series of useful reconstructed images. Each image of the second series of useful reconstructed images is formed by the square of the imaginary part of an image of a second series of reconstructed images.

The second series of reconstructed images is associated with a sampling step along the axis (Oz), less than the sampling step of the first series of reconstructed images. Each image of the second series of reconstructed images corresponds to the region of interest such as defined hereinabove. The amplitude of the sampling range along the axis (Oz) associated with the second series of reconstructed images, is less than the amplitude of the sampling range associated with the first series of reconstructed images. The second series of reconstructed images can be calculated solely for the searching of a precise position of the particle of interest.

The sub-steps 72, and 73 are implemented on the second series of useful reconstructed images, in order to calculate a precise position of the particle of interest, along the axis (Oz).

FIG. 750 corresponds to FIG. 730, by replacing the first series of useful reconstructed images with the second series of useful reconstructed images.

sub-step 76:

A precise position of the particle of interest is calculated, in a plane orthogonal to the axis (Oz).

For this, a selection is made from the images of the second series of useful reconstructed images, of that associated with the precise position of the particle of interest along the axis (Oz).

A thresholding is carried out on this image, in order to obtain a new binary image. Then, the coordinates of the centre of the binary object revealed by the thresholding are detected.

Many alternatives can be considered.

In particular, we can consider the embodiment such as described hereinabove, wherein we have:

H(u, v, z)=exp(i*2*π*z*w), with $$w = \sqrt{\frac{1}{\lambda^2} - u^2 - v^2},$$

for $$u^2 + v^2 \leq \frac{1}{\lambda^2}$$

H(u, v, z)=0 otherwise.

A useful reconstructed image is therefore defined as being the square of the modulus of the corresponding reconstructed image.

Then, steps similar to those described hereinabove are implemented, with the difference that searching for a position along the axis (Oz) implements the research of a useful reconstructed image having a maximum value for standard deviation.

According to another alternative, we can consider the embodiment such as described hereinabove, wherein we have:

H(u, v, z)=exp(i*2*π*z*w), with $$w = \sqrt{\frac{1}{\lambda^2} - u^2 - v^2},$$

for $$u^2 + v^2 \leq \frac{1}{\lambda^2}$$

H(u, v, z)=0 otherwise.

Each useful reconstructed image is then defined as being the square of the modulus of the corresponding reconstructed image.

An image of the gradients is then formed such as defined hereinabove, and, by thresholding, the approximate positions of the biological particles are deduced, in a plane orthogonal to the axis (Oz). The image obtained here by thresholding is called the first thresholded image. In particular the approximate position of the particle of interest is as such defined, in a plane orthogonal to the axis (Oz).

In the first thresholded image, a first binary object associated with a biological particle is arbitrarily selected. A first region of interest receiving this single binary object is defined.

Then, a region corresponding to this first region of interest is selected, in each useful reconstructed image. Using the series of images of the first region of interest created as such, the position along the axis (Oz) of the image that has the maximum standard deviation value is sought. This position defines an approximate position of the particle of interest, along the axis (Oz), assuming that all of the biological particles are located substantially in the same plane orthogonal to the axis (Oz).

Then, we return to the image of the gradients and a second thresholded image is formed, with a threshold greater than the threshold used to form the first thresholded image (for example 1.5 times greater). In the second thresholded image, the particle of interest is defined by arbitrarily choosing a second binary object. By searching for the centre of this second binary object, the precise position of the particle of interest is deduced, in a plane orthogonal to the axis (Oz).

Using this second thresholded image, a second region of interest receiving this single second binary object is defined. Then, a region is selected corresponding to this second region of interest, in each useful reconstructed image. Using the series of images created as such, the position along the axis (Oz) of the image that has a maximum standard deviation value is sought. This position defines a precise position of the particle of interest, along the axis (Oz).

FIG. 8 is used to show a particular case of the invention. Reference is made to the numerical references of FIG. 1.

In order to determine the distance between the particle of interest and the reference point, according to an axis parallel to the axis 135, the distance according to this axis is calculated, between the particle of interest and the object plane associated with the reference image.

In practice, the calculation makes it possible to determine the absolute value of the distance, according to an axis parallel to the axis 135, between the particle of interest and the object plane associated with the reference image. Then one or the other sign is selected knowing the experimental mounting.

For example, if the reference point is located above the upper interface 117, and if the object plane associated with the reference image is located above the upper interface 117, then it is known that the particle of interest is under the object plane associated with the reference image.

When it is not possible to determine with certainty the sign of this distance, a profile along the axis (Oz) relative to the real part of the reconstructed images can be used. The embodiment as described hereinabove can then be considered, wherein we have:

$$H(u,v,z)=\exp[-|z|*Im(p(u,v))+i*z*Re(p(u,v))]$$

In particular, the following steps can be implemented:

using the series of reconstructed images, a series of secondary images is determined, with each secondary image being formed by the real part of a corresponding reconstructed image;

in the same way as in sub-step 72 shown in FIG. 7, the series of secondary images (matrix with three dimensions) is transformed into a matrix with two dimensions, of which one dimension corresponds to the pixels, and the other dimension corresponds to an offset along the axis (Oz).

in said matrix with two dimensions, the pixels that have a strong gradient of intensity along the axis (Oz) are selected. An average gradient associated with these pixels is as such defined. It is this gradient which is shown in FIG. 8. The axis of the abscissa is an offset along the axis (Oz), in particular an offset of the object plane relatively to the position of the object plane associated with the reference image. The axis of the ordinates relates to the real part of the secondary images.

according to the form of the profile, it is determined the sign of the distance, according to an axis parallel to the axis 135, between the particle of interest and the object plane associated with the reference image:

if we move, for an increasing abscissa, from a positive maximum to a negative minimum (case of FIG. 8), the reference image is above the object plane (in the direction of propagation of the light), if we move, for an increasing abscissa, from a negative minimum to a positive maximum (opposite case of FIG. 8), the reference image is below the object plane (in the direction of propagation of the light).

The invention is not limited to the examples mentioned hereinabove, and many alternatives can be considered without leaving the scope of this invention. For example, step of the digital construction of a series of reconstructed images can implement propagation operators other than those mentioned in the example. The series of reconstructed images can also be exploited in different ways, in order to deduce the distance between the object plane associated with the reference image, and the particle of interest.

The invention claimed is:

1. A method for analyzing a sample receiving biological particles, among which is a particle of interest, the sample being arranged between a first light source and an optical system, the optical system carrying out an optical conjugation between an object plane and an image plane wherein is located an image sensor, and the sample being located inside a fluidic chamber delimited on a side of the image sensor by an upper slide, the method comprising:

illuminating a reference point located on a face of the upper slide by a laser beam focused by the optical system;

using the image sensor to receive an image of a spot formed by of the laser beam, wherein the laser beam, the image sensor, and the optical system are arranged such that a focusing point of the laser beam is in the object plane;

adjusting a distance, along an axis parallel to the optical axis of the optical system, between the sample located in the fluidic chamber and the optical system based upon the image and by detecting specular reflection of the laser beam on the upper slide, wherein the reference point is positioned in the object plane of the optical system when said specular reflection is detected;

offsetting the object plane of the optical system relatively to the reference point, along an axis parallel to the optical axis of the optical system, by a known distance as a useful distance, and so as to place the particle of interest outside of the object plane of the optical system;

using the first light source, illuminating of a region receiving the particle of interest, as an illuminated region;

using the image sensor, acquiring a holographic image of the illuminated region, as a reference image or defocused image;

using the reference image, digitally constructing a series of reconstructed images, each associated with a simulation of a predetermined offset of the object plane along the optical axis of the optical system; and using the series of reconstructed images, determining a distance along an axis parallel to the optical axis of the optical system, between the particle of interest and the object plane.

2. A method for analysis according to claim 1, wherein the offset of the object plane of the optical system relatively to the reference point is implemented by a translation of a support receiving the sample in its fluidic chamber, relatively to the optical system.

3. A method for analysis according to claim 1, further comprising determining a distance between the particle of interest and the reference point, using the distance between the particle of interest and the object plane and the useful distance.

4. A method for analysis according to claim 1, further comprising determining presence of the particle of interest using the distance between the particle of interest and the object plane.

5. A method for analysis according to claim 1, wherein the biological particles adhere to an interface of the sample, comprised of a lower or upper interface of the sample.

6. A method for analysis according to claim 1, wherein a distance along an axis parallel to the optical axis of the optical system, between the position of the object plane associated with the reference image, and the projection of the reference point according to the optical axis and on an upper interface of the sample, is between +5 µm and +2000 µm or between −5 µm and −2000 µm, the upper interface being defined by the boundary between the upper slide and the sample.

7. A method for analysis according to claim 1, wherein the illuminated region comprises a plurality of biological particles.

8. A method for analysis according to claim 1, wherein the first light source has a spectral width less than 200 nm.

9. A method for analysis according to claim 1, further comprising determining, using the series of reconstructed images, the position of the particle of interest in a plane orthogonal to the optical axis of the optical system.

10. A method for analysis according to claim 3, wherein each reconstructed image is formed by a real part and an imaginary part, and among the real and imaginary parts, only the imaginary parts of the reconstructed images are used to determine a distance along an axis parallel to the optical axis of the optical system, between the particle of interest and the reference point.

11. A method for analysis according to claim 1, wherein each reconstructed image is associated with an offset along the optical axis of the optical system and with a value of a useful parameter, so as to constitute a function that describes change in the useful parameter according to the offset, and wherein the determining of the distance between the particle and the object plane implements a search for a remarkable value of an extremum, or an inflection point, or a passage through zero of the function.

12. A method for analysis according to claim 1, wherein the determining of the distance between the particle of interest and the object plane comprises:
using a first series of reconstructed images associated with first simulated offsets of the object plane, determining an approximated distance between the particle of interest and the object plane; and
using a second series of reconstructed images associated with second simulated offsets of the object plane, with the second simulated offsets being finer than the first simulated offsets, determining a precise distance between the particle of interest and the object plane.

13. A method for analysis according to claim 1, wherein using the distance between the particle of interest and the object plane, the optical system is displaced in relation to the particle of interest so as to focus the analysis laser beam on the particle of interest.

14. A method for analysis according to claim 1, wherein using the distance between the particle of interest and the object plane, the optical system is displaced in relation to the particle of interest so as to adjust the focusing of the optical sensor located in the image plane of the optical system.

15. A method for analysis according to claim 1, further comprising counting the number of biological particles present in the sample.

16. A method for analysis according to claim 1, wherein the biological particles are selected from the group of bacteria, spores, cells, yeasts, or micro-organisms.

17. A device for analyzing a sample receiving biological particles, among which a particle of interest, comprising:
a first light source;
an imaging unit comprising an optical system and an image sensor, such that the image sensor is located in an image plane of the optical system, the image plane being a conjugate, by the optical system, of an object plane;
a support adapted to receive a fluidic chamber receiving the sample, arranged between the first light source and the imaging unit, an upper slide delimiting the fluidic chamber;
a laser, arranged to emit a laser beam focused by the optical system, and such that the image sensor receives an image of a spot formed by specular reflection of the laser beam on the upper slide, wherein the laser beam, the image sensor, and the optical system are arranged such that the focusing point of the beam is in the object plane;
means for translation, adapted to displace the support relatively to the optical system, along an axis parallel to the optical axis of the optical system; and
calculation means connected to a memory storing information relative to a reference point located on a face of the upper slide and configured to:
identify a relative position of the sample and of the optical system;
receive a holographic image acquired by the image sensor as a reference image, when the object plane is offset with respect to the reference point;
digitally construct, using the reference image, a series of reconstructed images, each reconstructed image associated with a simulation of a predetermined offset of the object plane along the optical axis of the optical system; and
determine a distance along an axis parallel to the optical axis of the optical system, between the particle of interest and the object plane.

* * * * *